United States Patent
Ferrie

(10) Patent No.: US 9,689,323 B2
(45) Date of Patent: Jun. 27, 2017

(54) METHOD FOR DETERMINING THE WATER CONTENT OF A MIXED ALCOHOL/GASOLINE FUEL IN AN INTERNAL COMBUSTION ENGINE, AND DEVICE FOR IMPLEMENTING SAME

(75) Inventor: Jean Paul Ferrie, Rieumes (FR)

(73) Assignees: CONTINENTAL AUTOMOTIVE FRANCE, Toulouse (FR); CONTINENTAL AUTOMOTIVE GMBH, Hannover (DE)

(*) Notice: Subject to any disclaimer, the term of this patent is extended or adjusted under 35 U.S.C. 154(b) by 1010 days.

(21) Appl. No.: 13/980,398

(22) PCT Filed: Jan. 17, 2012

(86) PCT No.: PCT/EP2012/000169
§ 371 (c)(1),
(2), (4) Date: Aug. 6, 2013

(87) PCT Pub. No.: WO2012/097974
PCT Pub. Date: Jul. 26, 2012

(65) Prior Publication Data
US 2013/0317724 A1    Nov. 28, 2013

(30) Foreign Application Priority Data
Jan. 20, 2011    (FR) ..................... 11 00163

(51) Int. Cl.
*F02D 41/00* (2006.01)
*G01N 27/12* (2006.01)
(Continued)

(52) U.S. Cl.
CPC ....... *F02D 41/0025* (2013.01); *F02D 19/084* (2013.01); *F02D 19/087* (2013.01);
(Continued)

(58) Field of Classification Search
CPC ...... F02D 41/0025; F02D 41/22; F02D 41/06; F02D 41/1454; F02D 19/084;
(Continued)

(56) References Cited

U.S. PATENT DOCUMENTS

| 4,905,655 A | * | 3/1990 | Maekawa | ........... F02D 19/0684 123/1 A |
| 2008/0295574 A1 | | 12/2008 | Miersch-Wiemers et al. | |

(Continued)

FOREIGN PATENT DOCUMENTS

| DE | 10 2006 029970 | 1/2008 |
| DE | 10 2007 057713 | 6/2009 |

(Continued)

OTHER PUBLICATIONS

International Search Report dated Apr. 17, 2012, corresponding to PCT/EP2012/000169.

*Primary Examiner* — Hieu T Vo
*Assistant Examiner* — Arnold Castro
(74) *Attorney, Agent, or Firm* — Young & Thompson

(57) ABSTRACT

Disclosed is a method for determination of the water content of a mixed alcohol/gasoline fuel in an internal combustion engine of a vehicle, which includes the stages of: determination of a first value for alcohol content of the fuel using a measurement of combustion richness; determination of a second value for alcohol content of the fuel using a measurement recorded by a sensor for measurement of the electrical conductivity of the fuel; comparison of the first value and the second value; and, when the first value is lower than the second value, determination of the water content of the fuel by assigning a predetermined value for water content associated with the pair consisting of the first value and of the second value for alcohol content.

20 Claims, 2 Drawing Sheets

(51) Int. Cl.
  *F02D 19/08* (2006.01)
  *F02D 41/06* (2006.01)
  *G01N 33/28* (2006.01)
  *F02D 41/14* (2006.01)
  *F02D 41/22* (2006.01)
  *G01N 27/06* (2006.01)

(52) U.S. Cl.
  CPC ........... *F02D 41/06* (2013.01); *G01N 27/121* (2013.01); *G01N 33/2847* (2013.01); *F02D 41/1454* (2013.01); *F02D 41/22* (2013.01); *F02D 2041/228* (2013.01); *F02D 2200/0611* (2013.01); *F02D 2250/14* (2013.01); *G01N 27/06* (2013.01); *Y02T 10/36* (2013.01)

(58) Field of Classification Search
  CPC ............... F02D 19/087; F02D 2250/14; F02D 2200/0611; F02D 2041/228; G01N 27/06; G01N 27/121; G01N 33/2847; Y02T 10/36
  See application file for complete search history.

(56) References Cited

U.S. PATENT DOCUMENTS

| | | |
|---|---|---|
| 2010/0036587 A1 | 2/2010 | Kato et al. |
| 2010/0050982 A1 | 3/2010 | Annoura |
| 2010/0126253 A1 | 5/2010 | Rosel et al. |
| 2011/0132340 A1* | 6/2011 | Soltis ............... F02D 41/0025 123/703 |
| 2011/0132342 A1* | 6/2011 | Soltis ............... F02D 41/0025 123/703 |

FOREIGN PATENT DOCUMENTS

| | | |
|---|---|---|
| DE | 10 2008 010555 | 8/2009 |
| EP | 2 042 719 | 4/2009 |

* cited by examiner

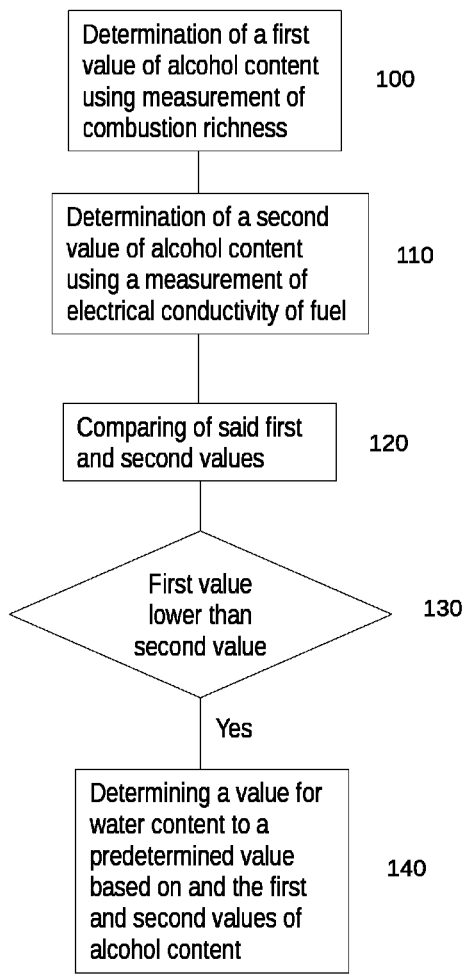

METHOD FOR DETERMINING THE WATER CONTENT OF A MIXED ALCOHOL/GASOLINE FUEL IN AN INTERNAL COMBUSTION ENGINE, AND DEVICE FOR IMPLEMENTING SAME

The present invention comes within the field of vehicles having a "flex-fuel" internal combustion engine, that is to say an engine which can be operated with different types of fuels comprising gasoline and alcohol in variable proportions. More particularly, the invention relates to a method for determination of the water content of a mixed alcohol/gasoline fuel in an internal combustion engine of a vehicle and to a device for the implementation of such a method. Another aspect of the invention is a more general method for regulating the operation of an internal combustion engine of a vehicle, including such a method for determining the water content.

BACKGROUND OF THE INVENTION

The number of flex-fuel vehicles in circulation is increasing.

The commonest type of alcohol participating in the makeup of the fuels currently provided on the market is ethanol. It is present therein in proportions which can vary according to the countries. In some countries, in particular in Brazil, the ethanol-based fuel commonly used exhibits a theoretical ethanol content of 100% and corresponds to the denomination E100.

Such E100 fuels are not, however, devoid of traces of water, due in particular to the hydrophilic nature of this alcohol. While water contents of these fuels of less than 5% are common and without significant consequence with regard to the operation of the engine, it frequently happens, depending on the storage conditions and time of the fuel, that this water content rises above this value, sometimes even up to 12 or 15%.

It is thus possible, in flex-fuel vehicles (FFVs), to have present a mixture of alcohol, gasoline and water, in variable respective contents, as a function of the type of residual fuel present in the tank when it is refilled and of the type of fuel introduced during this refilling.

In point of fact, the presence of an excessively large amount of water in the fuel furthermore comprising alcohol has harmful consequences with regard to the operation of an engine, in particular under "cold" operation conditions, that is to say conditions under which the temperature of the liquid coolant of the engine does not exceed 30° C. Mention may be made, by way of example, of an instability in combustion during the warmup of the engine which is effected in particular by the lighting of warning lights on the dashboard, ignition problems, impossibility of keeping the engine idling, a starting time increased by 3 to 20 seconds, the stalling of the engine under transient conditions, and the like. In the worst situations, it may be impossible to start the engine.

SUMMARY OF THE INVENTION

Knowing the water content in a mixed alcohol/gasoline fuel would make it possible to detect such risks of dysfunctioning of the engine and to correspondingly take measures, in particular by appropriately adjusting the stoichiometric characteristics of the startup and of the cold operation of the engine.

The present invention is based on the observation that the measurement of the alcohol content of an alcohol/gasoline mixture was disrupted by the presence of water in the fuel, this being in a way which can be varied with the water content of the fuel and not according to a predictable modeling law. The alcohol content is measured conventionally by a sensor for measurement of the electrical conductivity of the fuel. This measurement of the alcohol content did not make it possible, however, to evaluate the water content of the fuel when an alcohol/water/gasoline mixture was present.

The method according to the invention comprises the stages of:
  determination of a first value for alcohol content of the fuel using a measurement of combustion richness,
  determination of a second value for alcohol content of the fuel using a measurement recorded by a sensor for measurement of the electrical conductivity of the fuel,
  comparison of said first value and said second value,
  and, when said first value is lower than said second value, determination of the water content of the fuel by assigning a predetermined value for water content associated with the pair consisting of said first value and of said second value for alcohol content.

The method according to the invention thus advantageously employs means already used conventionally in existing vehicles, in particular a sensor for measurement of the combustion richness and a sensor for measurement of the electrical conductivity of the fuel. It makes use of the data recorded by these sensors to deduce therefrom a value for the water content of the mixed alcohol/gasoline fuel, by treatment of two values for alcohol content determined, in a way conventional per se, respectively from each of these two data. When it is apparent that these values for alcohol content are divergent, thus testifying to an abnormal presence of water in the fuel, this method then determines the water content of the fuel as being equal to a predetermined value associated with the specific pair of values for alcohol content thus obtained. This predetermined value for water content is drawn up prior to the implementation of the method, for example experimentally on an engine test rig during the development of an engine representative of mass production.

The method according to the invention can thus comprise a preliminary stage of the experimental drawing up of graphs associating, with each pair of values for ethanol content determined from the measurements carried out by the two sensors, a value for water content of the fuel.

According to preferred embodiments, the invention additionally corresponds to the following characteristics, implemented separately or in each of their technically effective combinations.

In preferred embodiments of the invention, the measurement of combustion richness is carried out in "hot" operation of the engine, so as to provide a result which is as reliable as possible with regard to the value for the alcohol content in the fuel which is deduced therefrom. In the context of the invention, an engine is regarded as operating "hot" when the temperature of the liquid coolant of the engine is greater than 70 or 80° C.

According to an advantageous characteristic of the invention, the measurement of combustion richness is carried out by means of a lambda probe positioned downstream of an exhaust manifold of the vehicle. Such a lambda probe is already used conventionally in many combustion engine vehicles to determine the combustion richness of the engine by measuring the oxygen content of the exhaust gases. Its operating principle is based, in brief, on the measurement of a current formed by the passage of the molecular oxygen ions through a porous body of the probe.

In preferred embodiments of the invention, the first value for alcohol content is determined from a measurement of combustion richness carried out after introduction, into a fuel tank of the vehicle, of a new volume of fuel and after stabilization of the combustion richness measured. As this stabilization testifies to the fact that the new fuel introduced has arrived at the injection harness of the vehicle, it is advantageously ascertained from this fact that the value for alcohol content then obtained is representative of this new fuel.

Preferably, the sensor for measurement of the electrical conductivity of the fuel is positioned at the inlet of an injection rail of the combustion engine or in said rail, with the result that information is drawn therefrom with regard to the fuel immediately before its injection. Corrective measures for the operation of the engine can thus advantageously be taken, in particular with regard to the amount of fuel injected, this being done virtually in real time and in the most suitable way possible for the water content of the fuel occurring in the injection rail.

According to a particularly advantageous characteristic of the invention, targeted at solving the problems of operation of the "cold" engine, in particular at startup and in the following phases, the first value for alcohol content is determined from a measurement of combustion richness carried out immediately before stopping the engine and is stored, and the second value for alcohol content is determined immediately after the subsequent startup of the engine. This is understood to mean that the first value for alcohol content taken into account is the value determined from the final measurement of combustion richness recorded before stopping the engine and that the second value for alcohol content taken into account is the value determined from the first measurement of the electrical conductivity of the fuel recorded after the subsequent startup of the engine.

The use of such respective values makes it possible to precisely determine the water content of the fuel ready to be injected into the engine, at the very startup, and consequently to take the most appropriate possible corrective measures for operation of the engine.

Preferably, the first measurement of the electrical conductivity of the fuel taken into account for the calculation of the second value for alcohol content is recorded from the time that an engine control unit of the vehicle is switched on, before even starting up the engine. Measurements are subsequently recorded continuously.

In "cold" operation of the engine, the second values for alcohol content thus successively recorded by the sensor are compared with the first value for alcohol content deduced from the final measurement of combustion richness recorded by the lambda probe before stopping the engine, this first value for alcohol content having been stored by the engine control unit of the vehicle before stopping the engine.

The method according to the invention proves in particular to be entirely advantageous in the configurations in which the alcohol content of the fuel is between approximately 30 and 90% and the water content is greater than approximately 5%.

The invention also relates to a device for the implementation of a method for determination of the water content of a mixed alcohol/gasoline fuel in an internal combustion engine of a vehicle as described above. This device comprises:

means for measurement of combustion richness, preferably a lambda probe, means for determination of a first value for alcohol content of the fuel from a measurement of the combustion richness recorded by these means for measurement of combustion richness, a sensor for measurement of the electrical conductivity of the fuel, means for determination of a second value for alcohol content of the fuel from a measurement recorded by this sensor for measurement of the electrical conductivity of the fuel, and means for comparison of said first value and said second value and for determination of the water content of the fuel by assigning a predetermined value for water content associated with the pair consisting of said first value and said second value for alcohol content.

The various means above participating in the make-up of this device are advantageously already used in many existing hybrid combustion engine vehicles, furthermore in an effective arrangement for the implementation of the method according to the invention. The device corresponding to the definition of the present invention consequently involves only a small additional expenditure for manufacturing and installing in the vehicle. It can in particular be summed up in a simple updating of the software executed by the engine control unit of the vehicle.

The various means for determination of the values for alcohol content from the measurements recorded, for comparison of these values and for determination of an associated water content can advantageously be incorporated in the control unit of the vehicle.

In preferred embodiments of the invention, the device additionally comprises means for storing the first value for alcohol content determined from a measurement of combustion richness carried out immediately before stopping the engine of the vehicle.

The determination, by means of the above method and device, of a water content of the fuel which is greater than a predetermined threshold value can in particular make it possible to alert the driver to the presence in the engine of a defective fuel. This warning sign can, for example, take the form of the lighting of a warning light on the dashboard.

The information with regard to this water content can also be used to adjust the operating parameters of the engine so as to avoid the problems which may be related thereto.

Thus, another aspect of the invention is a method for regulation of the operation of an internal combustion engine of a vehicle, which comprises the stages of:

determination of the water content of a mixed alcohol/gasoline fuel in the engine by a method as described above, and adjustment of the amount of fuel injected as a function of the value of the water content thus determined.

In preferred embodiments, the adjustment stage of this method is carried out at the startup of the vehicle and in the "cold" operation periods of the engine.

This adjustment is reflected by an increase in the amount of fuel injected when the water content of the fuel increases. It is carried out by means conventional per se.

Other operating parameters of the engine, such as the spark advance, the phasing of the injection or the opening of the throttle valve, can also be adjusted as a function of the determined water content of the fuel.

BRIEF DESCRIPTION OF THE DRAWINGS

FIG. 2 provides a flow chart of particular steps carried out in a method in accordance with a preferred embodiment of the invention.

DETAILED DESCRIPTION OF THE PREFERRED EMBODIMENTS

Figure 1:
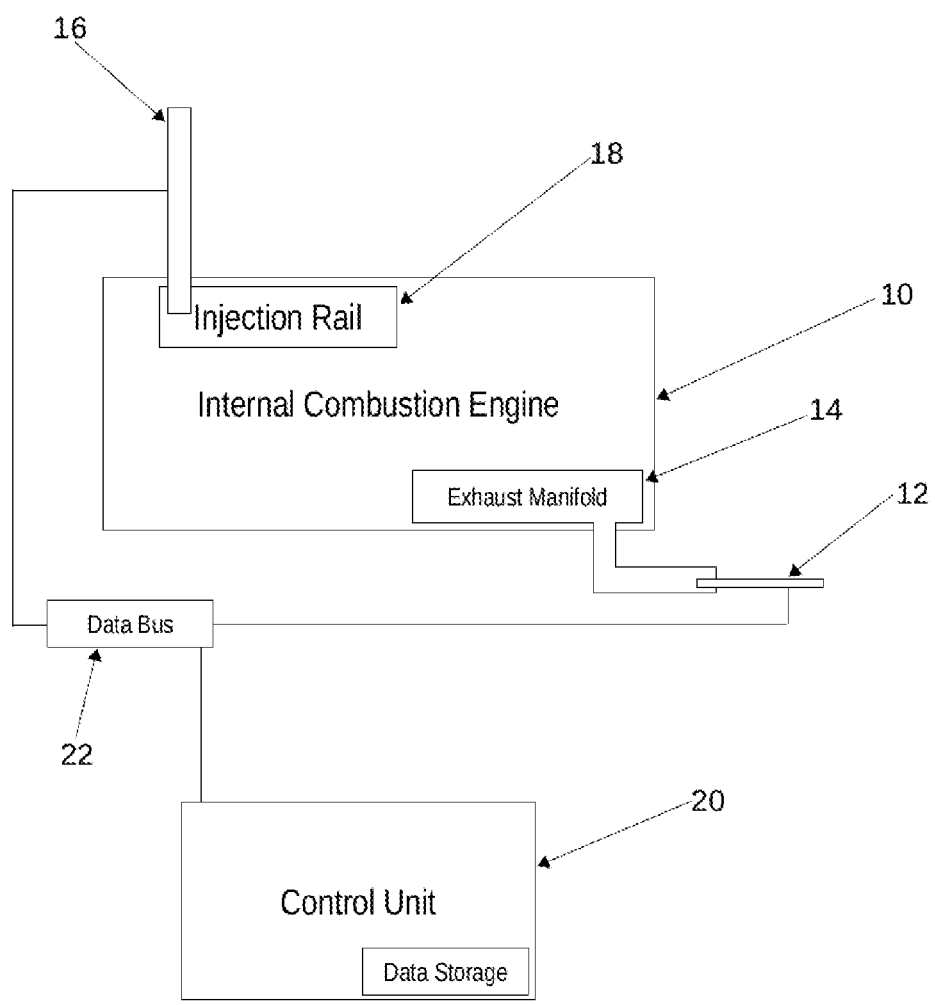
FIG. 1 provides a schematic drawing of basic structural components of a preferred embodiment of the invention.

The invention will now be described more specifically in the context of the implementational example below, which is in no way limiting thereof.

A device according to a preferred embodiment of the invention, for the implementation of a method for determination of the water content of a mixed ethanol/gasoline fuel in an internal combustion engine 10 of a vehicle is diagrammatically illustrated in FIG. 1:

- a lambda probe 12 positioned downstream of an exhaust manifold 14 of the internal combustion engine,
- a sensor 16 for measurement of the electrical conductivity of the fuel, positioned at the inlet of an injection rail 18 of the internal combustion engine 10 of the vehicle,
- means for the transfer of data respectively from the lambda probe and from the sensor for measurement of the electrical conductivity of the fuel to an engine control unit 20 of the vehicle, such as a data bus 22, this engine control unit 20 comprising:

- means for determination of a first value for ethanol content of the fuel from a measurement of combustion richness recorded by the lambda probe,
- means for storage of the first value for ethanol content determined from a measurement of combustion richness carried out immediately before stopping the engine of the vehicle,
- means for determination of a second value for ethanol content of the fuel from a measurement recorded by the sensor for measurement of the electrical conductivity of the fuel,
- means for comparison of the first value and of the second value for ethanol content,
- and means for determination of the water content of the fuel by assigning a predetermined value for water content associated with the pair consisting of the first value and of the second value for ethanol content.

The engine control unit 20 is preferably of the programmed computer type, comprising at least one microprocessor, and storage means (magnetic hard disk, flash memory, optical disk, and the like) in which a computer program is stored, in the form of a set of program code instructions to be executed in order to carry out the various calculation stages of the method for determination of the water content according to the invention. According to some embodiments, the calculation device also comprises one or more specialized integrated circuits, of FPGA (Field Programmable Gate Array), CPLD (Complex Programmable Logic Device), and the like, type, suitable for carrying out all or some of the calculation stages of the method.

In a preliminary stage, a method according to an embodiment of the invention comprises the experimental drawing up of a graph associating a value for water content of the fuel with each pair consisting of a first value for ethanol content and of a second value for ethanol content which are given by the abovementioned means of determination.

By way of example, for a first value for ethanol content, such as determined from a measurement of combustion richness recorded by the lambda probe, equal to 70%, the following table 1 is thus drawn up, in which a value for water content is associated with each second value for ethanol content, as determined from a measurement of electrical conductivity of the fuel:

TABLE 1

Values for water contents associated with each given "first value for ethanol content equal to 70%-second variable value for ethanol content" pair

| Second value for ethanol content measured (%) | 81 | 86 | 87 | 89 |
|---|---|---|---|---|
| Associated value for water content of the fuel (%) | 4.9 | 7 | 7.7 | 8.4 |

In a preferred embodiment of the method according to the invention, which is in no way limiting thereof, an exemplary flow chart provided in FIG. 2, when the driver comes to fill up the vehicle, for example by introducing E100 fuel into a tank which already contains a residual amount of gasoline, measurements of combustion richness are acquired by means of the lambda probe (100) until the measured combustion richness is observed to stabilize, which testifies to the fact that the new fuel, comprising gasoline, ethanol and potentially water, has arrived at the injector. Once this stabilization is obtained, successive measurements of combustion richness are acquired at regular intervals by means of the lambda probe and successive values for ethanol content in the fuel are deduced therefrom according to calculations within the competence of a person skilled in the art.

The final value, thus determined immediately before stopping the engine, is stored in the control unit of the vehicle. By way of example, this value is equal to 70%.

On subsequently starting up the engine or, better still, from the time that the engine control unit of the vehicle is switched on prior to this startup, a measurement of the electrical conductivity (110) is acquired by means of the sensor for measurement of the electrical conductivity of the fuel and a second value of ethanol content of the fuel is deduced therefrom, for example equal to 86%, by calculations within the competence of the person skilled in the art.

The two values for content of fuel thus obtained are compared (120), (130). As these values are divergent, the water content of the fuel is determined by assigning the predetermined value associated with the "70%-86%" pair, by means of the above table 1 (140).

It is thus determined that the water content of the fuel is equal to 7%.

From this information, a method for the regulation of the operation of an engine according to the invention provides for the adjusting of the amount of fuel injected during the "cold" operation and transient phases of the engine, to take into account a significant presence of water in the fuel and to avoid dysfunctionings of the engine. This injected amount of fuel is determined by calculations which are within the scope of a person skilled in the art, insofar as by virtue of the present invention a person skilled in the art now has available a precise and reliable estimation of the water content of the fuel reaching the injector.

The above description clearly illustrates that, by its different characteristics and their advantages, the present invention achieves the objectives which it has been set. In particular, it provides a method and a device for the determination of the water content of a mixed alcohol/gasoline fuel in an internal combustion engine of a vehicle which are respectively simple to carry out and simple in makeup and which provide an effective tool for overcoming the problems of dysfunctioning, in particular under cold conditions, of the engine in the presence of a significant amount of water in the fuel. In particular, this method and this device require, in particular for the implementation and the use respectively thereof, only very few modifications of the current systems installed in the vehicles and are consequently associated only with a low additional cost.

The invention claimed is:

1. A method for determination of the water content of a mixed alcohol/gasoline fuel in an internal combustion engine of a vehicle, comprising:
   determining a first value for alcohol content of the fuel using a measurement of combustion richness;
   determining a second value for alcohol content of the fuel using a measurement recorded by a sensor for measurement of the electrical conductivity of the fuel;
   comparing said first value and said second value; and
   upon a determination that said first value is lower than said second value, determining the water content of the fuel by assigning a predetermined value for water content associated with the pair consisting of said first value and of said second value for alcohol content.

2. The method as claimed in claim 1, wherein the measurement of combustion richness is carried out in "hot" operation of the engine.

3. The method as claimed in claim 2, wherein the measurement of combustion richness is carried out by means of a lambda probe positioned downstream of an exhaust manifold of the vehicle.

4. The method as claimed in claim 2, wherein the first value for alcohol content is determined from a measurement of combustion richness carried out after introduction, into a fuel tank of the vehicle, of a new volume of fuel and after stabilization of the combustion richness measured.

5. The method as claimed in claim 2, wherein the sensor for measurement of the electrical conductivity of the fuel is positioned at the inlet of an injection rail of the internal combustion engine or in said rail.

6. The method as claimed in claim 2,
   wherein the first value for alcohol content is determined from a measurement of combustion richness carried out immediately before stopping the engine and is stored, and
   wherein the second value for alcohol content is determined immediately after the subsequent startup of the engine.

7. The method as claimed in claim 1, wherein the measurement of combustion richness is carried out by means of a lambda probe positioned downstream of an exhaust manifold of the vehicle.

8. The method as claimed in claim 7, wherein the first value for alcohol content is determined from a measurement of combustion richness carried out after introduction, into a fuel tank of the vehicle, of a new volume of fuel and after stabilization of the combustion richness measured.

9. The method as claimed in claim 7, wherein the sensor for measurement of the electrical conductivity of the fuel is positioned at the inlet of an injection rail of the internal combustion engine or in said rail.

10. The method as claimed in claim 7,
    wherein the first value for alcohol content is determined from a measurement of combustion richness carried out immediately before stopping the engine and is stored, and
    wherein the second value for alcohol content is determined immediately after the subsequent startup of the engine.

11. The method as claimed in claim 1, wherein the first value for alcohol content is determined from a measurement of combustion richness carried out after introduction, into a fuel tank of the vehicle, of a new volume of fuel and after stabilization of the combustion richness measured.

12. The method as claimed in claim 11, wherein the sensor for measurement of the electrical conductivity of the fuel is positioned at the inlet of an injection rail of the internal combustion engine or in said rail.

13. The method as claimed in claim 11,
    wherein the first value for alcohol content is determined from a measurement of combustion richness carried out immediately before stopping the engine and is stored, and
    wherein the second value for alcohol content is determined immediately after the subsequent startup of the engine.

14. The method as claimed in claim 1, wherein the sensor for measurement of the electrical conductivity of the fuel is positioned at the inlet of an injection rail of the internal combustion engine or in said rail.

15. The method as claimed in claim 14,
    wherein the first value for alcohol content is determined from a measurement of combustion richness carried out immediately before stopping the engine and is stored, and
    wherein the second value for alcohol content is determined immediately after the subsequent startup of the engine.

16. The method as claimed in claim 1,
    wherein the first value for alcohol content is determined from a measurement of combustion richness carried out immediately before stopping the engine and is stored, and
    wherein the second value for alcohol content is determined immediately after the subsequent startup of the engine.

17. A device for the implementation of a method as claimed in claim 1, comprising:
    means for measurement of combustion richness,
    means for determination of a first value for alcohol content of the fuel from a measurement of the combustion richness recorded by said means for measurement of combustion richness,
    a sensor for measurement of the electrical conductivity of the fuel,
    means for determination of a second value for alcohol content of the fuel from a measurement recorded by said sensor for measurement of the electrical conductivity of the fuel,
    means for comparison of said first value and said second value, and in the event that said first value is lower than said second value, determination of the water content of the fuel by assigning a predetermined value for water content associated with the pair consisting of said first value and said second value for alcohol content.

18. The device as claimed in claim 17, further comprising:
    means for storing the first value for alcohol content determined from a measurement of combustion richness carried out immediately before stopping the engine of the vehicle.

19. A method for regulation of the operation of an internal combustion engine of a vehicle, comprising:
    determining the water content of a mixed alcohol/gasoline fuel in the engine by a method as claimed in claim 1,
    adjusting the amount of fuel injected as a function of the value of the water content thus determined.

20. The method as claimed in claim 19, wherein said adjustment stage is carried out at the startup of the vehicle and in the "cold" operation periods of the engine.

* * * * *